United States Patent [19]

Nofre et al.

[11] Patent Number: 4,997,667

[45] Date of Patent: Mar. 5, 1991

[54] PYRIDINYL COMPOUNDS OF N-CARBAMOYL-N-THIOCARBAMOYL- OR N-AMIDINO-GLYCINE OR BETA-ALANINE USEFUL AS SWEETENING AGENTS

[75] Inventors: Claude Nofre, Lyons; Jean M. Tinti, Meyzieu; Farroudja O. Chatzopoulos, Saint Etienne, all of France

[73] Assignee: Univesite Claude Bernard, France

[21] Appl. No.: 285,602

[22] Filed: Dec. 16, 1988

[30] Foreign Application Priority Data

Dec. 18, 1987 [FR] France ............... 87 18114

[51] Int. Cl.$^5$ ............ C07D 271/12; C07D 239/28; A23L 1/236
[52] U.S. Cl. ...................... 426/548; 426/3; 426/556; 426/590; 426/660; 426/804; 424/48; 424/49; 424/64; 546/307; 546/309; 546/289
[58] Field of Search ............ 546/286, 307, 289; 514/352; 426/548, 3, 556, 500, 660, 804; 424/48, 49, 64

[56] References Cited

U.S. PATENT DOCUMENTS

| | | |
|---|---|---|
| 3,492,131 | 1/1970 | Schlatter ............ 426/548 |
| 3,642,491 | 2/1972 | Schlatter ............ 426/548 |
| 3,714,139 | 1/1973 | Schlatter ............ 426/548 |
| 3,800,046 | 3/1974 | Schlatter ............ 426/168 |
| 4,426,521 | 1/1984 | Tanaka et al. ........ 544/146 |
| 4,656,678 | 2/1987 | Nofre et al. ......... 426/548 |
| 4,673,582 | 6/1973 | Nofre et al. ......... 426/548 |

FOREIGN PATENT DOCUMENTS 0241395 10/1987 European Pat. Off. ........... 426/548

OTHER PUBLICATIONS

Chemische Berichte, vol. 94, No. 7, 1961 pp. 1814–1824, Weinheim, DE; F. Micheel et al. with translation.
Jeseph W. Tsang et al., Peptide Sweetners, 6. Structural Studies on the C-Terminal Amino Acid of L-Aspartyl Dipeptide Sweetner, American Chemical Society, Jan. 3, 1984, 6 pages.
Journal of Agricultural and Food Chemistry, vol. 28, No. 6, 1980, pp. 1338–1340.
Tinti, J. M. et al., Sweet Taste Receptor, Naturwissenschaften 67, Jan. 2, 1980, pp. 193–194.
Miller, et al., A Facile Conversion of Amino Acids to Guanidinio Acids, Communications, Sep. 1986, pp. 777–779.

Primary Examiner—Mary C. Lee
Assistant Examiner—Zinna Northington-Davis
Attorney, Agent, or Firm—Parkhurst, Wendel & Rossi

[57] ABSTRACT

Sweetening agents of the formula:

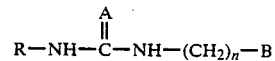

wherein R is an heterocyclic group which, in a preferred embodiment, is a 2-cyanopyrid-5-yl or 2-cyanopyrimidin-5-yl group, A is O, NH or NCN, NH being able to be satisfied in hydrochloride form, n is 1 or 2 and B is COOH or a sodium, potassium, ammonium, calcium or magnesium salt.

9 Claims, No Drawings

PYRIDINYL COMPOUNDS OF N-CARBAMOYL-N-THIOCARBAMOYL- OR N-AMIDINO-GLYCINE OR BETA-ALANINE USEFUL AS SWEETENING AGENTS

The present invention relates to new sweetening agents, which are useful in particular for sweetening foods, beverages, confectioneries, pastries, chewing gum, hygiene products, cosmetics, toiletries, pharmaceutical and veterinary products and their equivalents. It also relates to preparations and compositions containing such sweetening agents.

Among the chemical compounds presenting sweetening properties, "suosan" and its derivatives constitute a chemical series which has been widely studied since their discovery in 1948 by Petersen and Miller (Chem. Ber., 1948, 81, 31-38; see, for example, Beets, Structure-Activity Relationships in Human Chemoreception, Applied Science Publ., London, 1978, pp. 336-337; Crosby and Wingard, Developments in Sweeteners, Applied Science Publ., London 1979, p. 160; Tinti, Nofre and Peytavi, Z. Lebensm. Unters. Forsch., 1982, 175, 266-268) However, these compounds have never been used in practice as certain of them release potentially toxic molecules; this is the case of "suosan" which leads to 4-nitroaniline. Moreover, these compounds are only slightly soluble in solutions at acid pH (pH 2.5 to 3), and thus under usual conditions of utilization of synthetic sweetening agents in carbonated beverages ("soft drinks") which at present constitute the main market for sweeteners In U.S. Pat. application Ser No. 836,071, U.S. Pat. No. 4,877,895 the inventors described as new sweetening agents, compounds of the formula:

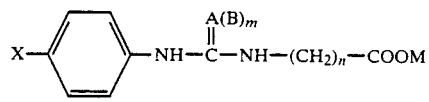

wherein:
A is N, N+ or C, N+ being able to be salified by Cl−;
m is 1 when A is N, and is 2 when A is N+ or C;
n is 1 or 2;
B, when n equals 1, is:
 CN,
 H,
 $NO_2$,
 $OCH_3$ or
 $SO_2R$, R being an alkyl, cycloalkyl or aryl group having up to 10 carbon atoms, 1 or 2 carbon atoms being able to be replaced by 1 or 2 sulfur or oxygen atoms, or when n equals 2, is:
 CN,
 H or
 $OCH_3$;
X, when B is CN, H or $OCH_3$, is:
 CN or
 $NO_2$, or when B is $NO_2$ or $SO_2R$, is:
 Cl,
 CN,
 $COCH_3$,
 F,
 H or
 $NO_2$; and
M is:
 H,
 Na,
 K,
 $NH_4$,
 ½ Ca or
 ½ Mg.

As was already the case for suosan and its derivatives, the compounds described in U.S. Pat. application Ser. No. 836,071, now U.S. Pat. No. 4,877,895 are insufficiently soluble in water at acid pH (pH 2.5 to 3) to be able to contemplate the use thereof in carbonated beverages ("soft drinks") which constitute the main market for synthetic sweeteners.

The present invention relates to sweetening agents of the formula:

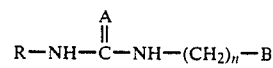

wherein:
R is an heterocyclic group which can be monocyclic or bicyclic,
 the monocyclic group being selected from the group consisting of:

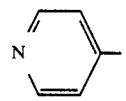

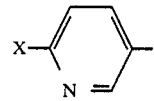

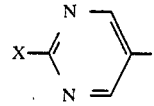

wherein
X is:
 Cl,
 CN or
 $NO_2$,
the bicyclic group being selected from the group consisting of:

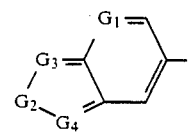

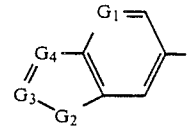

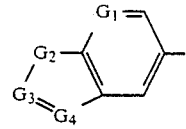

wherein:
G$_1$ is CH or N,
G$_2$ is CH$_2$, CO, NH, NCH$_3$, O or S,
G$_3$ and G$_4$ are CH, CCH$_3$, N or NO;
A is O, S, NH or N-CN, NH being able to be salified in hydrochloride form;
n is 1 or 2; and
B is COOH or a sodium, potassium, ammonium, calcium or magnesium salt.

In other words, the compounds of the present invention are distinguished from suosan or its derivatives and from the compounds described in U.S. Pat. application Ser. No. 836,071, U.S. Pat. No. 4,877,895 by the replacement of the carbocyclic group X-C$_6$H$_4$ by an heterocyclic group R, which has the effect of increasing their solubility in water under acid conditions, and therefore at the pH levels used in carbonated beverages (pH 2.5 to 3). In addition, the replacement of a carbocyclic group X-C$_6$H$_4$ by an heterocyclic group R modifies the sweetening potency of the compounds only slightly, which is totally unexpected in view of the knowledge that any modification, even slight, of the molecular structure of a sweetening agent often causes suppression of the sweetening character, the relationships between the structure and the sweetening activity effectively being unpredictable (M.G.J. BEETS, Structure-Activity Relationships in Human Chemoreception, Applied Science Publ., London, 1978, pp. 259–362; H. VAN DER WEL, A. VAN DER HEIJDEN, H. G. PEER, Food Reviews International, 1987, 3, 193–268)

Advantageously, in the sweetening agents according to the invention:
R is a 2-cyanopyrid-5-yl or 2-cyanopyrimidin-5-yl group;
A is 0 or NH;
n is 1 when A is NH or 2 when A is 0.

The invention also relates to the process which comprises sweetening foods, beverages, confectioneries, pastries, chewing gum, hygiene products, cosmetics, toiletries, pharmaceutical and veterinary products and their equivalents, by adding thereto an adequate quantity of one or more sweetening agents according to the present invention. By "adequate quantity" we mean a quantity of sweetening agent sufficient to produce the perception of a sweet taste.

The invention also relates to preparations which have been sweetened according to the process of the present invention.

The invention also relates to the sweetening compositions comprising an adequate quantity of at least one sweetening agent according to the present invention, and an appropriate carrier or bulking agent.

The invention also relates to sweetening compositions comprising an adequate quantity of one or more sweetening agents according to the present invention, and one or more other sweetening agents.

The products amenable to being sweetened by the sweetening agents of the present invention comprise all the products for which a component with sweet taste is desired, notably, and without limitation, food products (for human or animal consumption), beverages (alcoholic beverages, non-alcoholic beverages, juices, carbonated beverages), confectioneries, pastries, chewing gum, hygiene products, cosmetics, pharmaceutical and veterinary products and their equivalents.

The sweetening agents of the present invention can be added in pure form to comestible products to impart a sweet taste thereto. Nevertheless, by virtue of the high sweetening potency of the present sweetening agents, they are generally admixed with an appropriate carrier or bulking agent. Advantageously, the appropriate carriers or bulking agents are selected from the group consisting of polydextrose, starch, maltodextrins, cellulose, methylcellulose, carboxymethylcellulose, hydroxymethylcellulose, microcrystalline cellulose, sodium alginate, pectins, gums, lactose, maltose, glucose, leucine, glycerol, mannitol, sorbitol, sodium bicarbonate, phosphoric, citric, tartaric, fumaric, benzoic, sorbic and propionic acids, and their sodium, potassium and calcium salts and equivalents thereof.

The present sweetening agents can be employed in a comestible product alone, as the sole sweetening agent, or in the form of mixtures of two or more sweetening agents of the present invention. The present sweetening agents can also be used in combination with other sweetening agents such as the sugars (sucrose), corn syrup, fructose, sweet dipeptide derivatives (aspartame, alitame), neohesperidin dihydrochalcone, hydrogenated isomaltulose, stevioside, L-sugars, glycyrrhizin, xylitol, sorbitol, mannitol, acesulfame-K, saccharin or its sodium, potassium, ammonium or calcium salts, cyclamic acid and its sodium, potassium, ammonium or calcium salts, trichlorogalactosucrose, monellin, thaumatin and equivalents thereof.

The process for preparation of the sweetening agents of the present invention varies depending on whether A is 0, S, NH or NCN in the formula of the sweetening agent which is desired to be obtained.

The process comprises reacting:

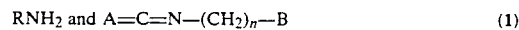
RNH$_2$ and A=C=N—(CH$_2$)$_n$—B                     (1)

when A is 0, the reaction being effected in an organic solvent such as acetonitrile or chloroform at room temperature or at boiling, or
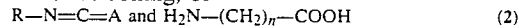
R—N=C=A and H$_2$N—(CH$_2$)$_n$—COOH              (2)

when A is 0 or S, the reaction being effected in water at room temperature, R—N=C=A being dissolved beforehand in an organic solvent such as benzene or chlorobenzene, or

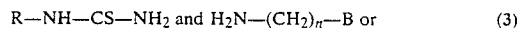
R—NH—CS—NH$_2$ and H$_2$N—(CH$_2$)$_n$—B or       (3)

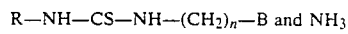
R—NH—CS—NH—(CH$_2$)$_n$—B and NH$_3$ when A is NH, or

R—NH—CS—NH—(CH$_2$)$_n$—B and H$_2$NCN when A is NCN, the reactions being effected at room temperature or at boiling in the presence of a condensation agent such as dicyclohexylcarbodiimide, or

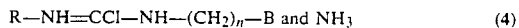
R—NH=CCl—NH—(CH$_2$)$_n$—B and NH$_3$              (4)

when A is NH, R—NH CCl—NH—(CH$_2$)$_n$—B being obtained by condensation of R—N=CCl$_2$ with H$_2$N—(CH$_2$)$_n$—B in chloroform or ethyl acetate at room temperature, the reaction mixture being heated to 70° C. for the condensation with NH$_3$, or

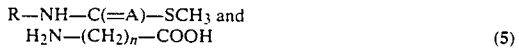
R—NH—C(=A)—SCH$_3$ and
H$_2$N—(CH$_2$)$_n$—COOH                              (5)

when A is NH or NCN, the reaction being effected in an ethanol-water mixture at boiling in the presence of a base such as NaOH or N(C$_2$H$_5$)$_3$, or R—H—(CH$_2$)$_n$—B and HCl in water (6)

when A is NH, the hydrolysis being effected at 70° C.

In the formulas of the reagents used, R and n correspond to the definitions given hereinbefore, B corresponds to a protected carboxyl group, for example in the form of an ester (methyl, ethyl, tert-butyl, benzyl ester), the protective group subsequently being eliminated by the most appropriate means, which may be, for example, saponification by NaOH or hydrolysis by HCl.

To obtain the compounds of the invention, the choice among processes (1) to (6) will be made by those skilled in the art as a function of the nature of A, R and B, of the value of n and of the experimental conditions specific to each of the processes.

The compounds of the invention can exist in acid form or in the form of a salt. They can therefore be salified by physiologically acceptable inorganic or organic bases or, in the compounds in which A is NH, by physiologically acceptable inorganic or organic acids. One of the methods of choice for preparing these salts comprises concentrating to dryness under vacuum a mixture, in aqueous solution, of a compound of the invention and one equivalent of a base or of an inorganic or organic acid. The preferred salts of the invention are the sodium, potassium, ammonium, calcium and magnesium salts or, when A is NH, the hydrochlorides.

The purification of the compounds of the invention was realized by standard techniques such as recrystallization, chromatography and the like Their purity and their structures were checked by the classical techniques such as thin-layer chromatography, high-performance liquid chromatography, infrared spectrometry, nuclear magnetic resonance and elemental analysis.

The sweetening potency of the compounds thus prepared was evaluated by a group of eight experienced human tasters For this purpose, the compounds, in aqueous solution in various concentrations, are compared in terms of taste with a control solution of sucrose in a concentration of 2% and in certain cases of 5% and 10%, i.e., in concentrations corresponding to those used in a common application. The sweetening potency of the synthetic sweetening agents actually varies as a function of the concentration of the sucrose solution used as a reference. The sweetening potency of the compound tested by comparison with sucrose then corresponds to the weight ratio which exists between the compound and sucrose at equal sweetening intensity, i.e., when the sweet tastes of the solutions of the tested compound and of the control solution of sucrose are considered by a majority of tasters to have the same sweetening intensity.

The sweetening agents of the present invention have the advantage that they can be added to any comestible product to which it is desired to impart a sweet taste, provided they are added in proportions sufficient to attain the desired level of sweetness The optimum utilization concentration of the sweetening agent will depend on diverse factors such as, for example, the sweetening potency of the sweetening agent, the conditions of storage and utilization of the products, the particular constituents of the products, the flavor profile of the comestible products and the desired level of sweetness. Any person skilled in the art can easily determine the optimum proportion of sweetening agent which must be employed to obtain a comestible product by conducting routine sensory analyses, i.e., taste tests. The preferred sweetening agents of the present invention are generally added to comestible products in proportions of about 0.001 to about 0.02 weight percent of the comestible product. The concentrated products obviously will contain higher percentages of sweetening agent(s), and will then be diluted according to the ultimate utilization purposes.

A very important advantage of the sweetening agents of the present invention is to provide in many cases a sweet taste very close to that of sucrose, notably without liquorice aftertaste (as is the case, for example, for glycyrrhizin or thaumatin) and without metallic or bitter aftertaste (as is the case, for example, for saccharin or acesulfame-K).

The heterocyclic derivatives described in the present invention, while definitely having a stability under acid conditions comparable to that of their carbocyclic analogs described in the prior art (Z. Lebensm Unters. Forsch., 1982, 175, 266-268) and in U.S. Pat. application Ser. No. 836,071, have the advantage, as already stated, of being much more soluble in water, as the comparative studies of their solubilities has successfully demonstrated.

The solubility was measured in the following manner. An excess of the compound, the solubility of which is to be determined, is placed in suspension in water at pH 3 (phosphate buffer) and at a temperature close to 0° C. (which corresponds to the conditions of preparation and of storage of carbonated beverages). The suspension, still in an ice bath, is then subjected to the action of ultrasound for 60 minutes and thereafter is filtered (through a Millipore Millex-HV filter, 0.45 micron). The compound, which as a result is dissolved to saturation in the filtrate, is analyzed by high-performance liquid chromatography (HPLC) relative to a reference solution of known concentration.

In this way it was observed, for example, that the compound described in Example 4 of the present application (in which compound R is a 2-cyanopyrid-5-yl group) has a solubility of about 400 mg/liter at 0° C., whereas its 4-cyanophenyl carbocyclic analog (Example 16 described in Z. Lebensm. Unters. Forsch., 1982, 175, 266-268) has a solubility of only about 100 mg/liter under the same conditions, the solubility of the heterocyclic derivative therefore being about 4 times higher than that of its carbocyclic analog. Similarly, it was observed, for example, that the compound described in Example 10 of the present application (in which compound R is a 5-benzofurazanyl group) has a solubility of about 1150 mg/liter at 0° C., i.e., about 2.8 times higher than that of the 4-nitrophenyl carbocyclic compound (Example 3 of U.S. Pat. application Ser. No. 836,071), which is about 410 mg/liter.

The manner in which the invention can be realized and the advantages which derive therefrom will be understood more clearly and will be further explained by, but not limited to, the practical examples which follow.

EXAMPLE 1

Synthesis of 4-pyridylcarbamoyl-beta-alanine:

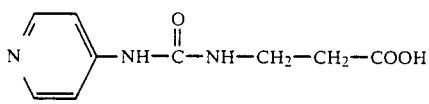

A solution of 1 g (10.64 mmol) of 4-aminopyridine and 2.3 g (15.9 mmol) of beta-alanine ethyl ester isocyanate in 30 ml of anhydrous acetonitrile is agitated for 20 hr at room temperature. After concentration to dryness and trituration of the resulting oily residue in ether (4 × 20 ml), 2.5 g (yield 88%) of 4-pyridylcarbamoyl-beta-alanine ethyl ester is obtained in the form of a solid having a melting point of 95° C.

A solution of 2 g (8.4 mmol) of 4-pyridylcarbamoyl-beta-alanine ethyl ester and 0.37 g (9.2 mmol) of sodium hydroxide in 50 ml of methanol and 0.1 ml of water is kept agitated for 24 hr at room temperature. After concentration to dryness, the resulting oily residue is taken up in 15 ml of water. After washing with 3 x 10 ml of dichloromethane, the aqueous phase is acidified with a 3 N hydrochloric acid solution until a pH close to 3 is obtained. The precipitate formed is filtered, washed with 10 ml of cold water and then dried 1.36 g (yield 95%) of 4-pyridylcarbamoyl-beta-alanine is obtained in the form of a solid having a melting point of 222° C.

The sweetening potency of this compound corresponds approximately, on a weight basis, to 50 (fifty) times that of sucrose (by comparison with a 2% sucrose solution).

EXAMPLE 2

Synthesis of 2-chloro-5-pyridylcarbamoyl-beta-alanine:

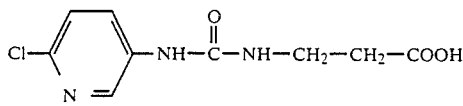

A solution of 2 g (12.9 mmol) of 2-chloro-5pyridyl isocyanate dissolved in 25 ml of benzene is added to a solution of 25 ml of water containing 1.26 g (14.2 mmol) of beta-alanine and 0.75 g (7 mmol) of sodium carbonate. Vigorous agitation is maintained for 1 hour at room temperature, after which the mixture is extracted with 3 × 50 ml of ethyl ether. The aqueous phase is cooled and then acidified with a 3 N hydrochloric acid solution until a pH of about 3 is obtained The precipitate formed is filtered, washed with 10 ml of cold water and then dried. 1.5 g (yield 45%) of 2-chloro-5-pyridylcarbamoyl-beta-alanine is obtained in the form of a solid having a melting point of 200° C.

The sweetening potency of this compound corresponds approximately, on a weight basis, to 50 (fifty) times that of sucrose (by comparison with a 2% sucrose solution).

EXAMPLE 3

Synthesis of N-[2-chloro-5aminopyridyl(imino)methyl]-2-aminoethanoic acid:

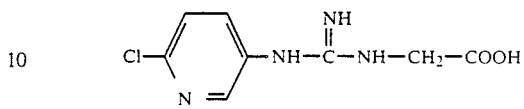

A solution of 1.2 g (6.4 mmol) of 2-chloro-5pyridylthiourea, 1 g (7.68 mmol) of glycine tert-butyl ester and 1.45 g (7.04 mmol) of dicyclohexylcarbodiimide in 30 ml of ethyl acetate is heated for 2.5 hr at 60° C. The dicyclohexylthiourea precipitate formed is eliminated by filtration. The filtrate is concentrated to dryness The product obtained is taken up in 20 ml of dichloromethane and then extracted with a 0.25 N aqueous hydrochloric acid solution (4 × 30 ml). The acid solution is then neutralized with a 1 N sodium hydroxide solution, and thereafter is extracted with dichloromethane (3 × 20 ml), thus permitting 0.65 g (yield 36%) of tert-butyl N-[2-chloro-5-aminopyridyl(imino)methyl]-2-aminoethanoate to be obtained in the form of an oil.

0.65 g (2.3 mmol) of the ester thus obtained is dissolved in 1.5 ml of glacial acetic acid and 3.2 ml (2.3 mmol) of a 7 N solution of hydrochloric acid in dioxane. After 1.5 hr at room temperature, the solvents are eliminated under reduced pressure The residue is taken up in ethyl ether (4 × 20 ml) and then dissolved in 15 ml of a saturated aqueous sodium carbonate solution. After washing with dichloromethane (3 × 10 ml), the aqueous phase is acidified with 3 N hydrochloric acid until a pH of 4 is obtained. The precipitate formed is filtered, and thereafter is washed with 5 ml of water and dried 0 11 g (yield 21%) of N-[2-chloro-5-aminopyridyl(imino)-methyl]-2aminoethanoic acid is obtained in the form of a solid having a melting point of 240° C.

The sweetening potency of this compound corresponds approximately, on a weight basis, to 50 (fifty) times that of sucrose (by comparison with a 2% sucrose solution).

EXAMPLE 4

Synthesis of 2-cyano-5-pyridylcarbamoyl-beta-alanine:

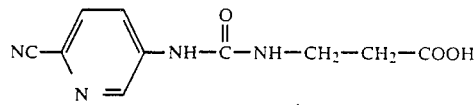

This compound is obtained in monohydrated form from beta-alanine and 2-cyano-5-pyridyl isocyanate by following the experimental procedure described in Example 2 (yield 24%, melting point 173° C.).

The sweetening potency of this compound corresponds approximately, on a weight basis, to 700 (seven hundred) times that of sucrose (by comparison with a 2% sucrose solution).

EXAMPLE 5

Synthesis of 2-cyano-5-pyrimidinylcarbamoyl-beta-alanine:

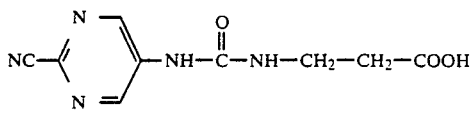

A solution of 0.83 g (7 mmol) of 2-cyano-5aminopyrimidine and 1 g (7 mmol) of beta-alanine ethyl ester isocyanate in 30 ml of anhydrous acetonitrile is heated for 4 hr at 70° C. The reaction mixture is concentrated to dryness and the residue is subjected directly to hydrolysis with 0.1 N HCl (50 ml) for 3 hr at 70° C. After cooling, the solution is treated with NaOH until a pH of 10 is obtained, washed with 3 × 40 ml of dichloromethane, acidified with HCl until a pH of 3 is obtained, and then concentrated to dryness in vacuum. The residue is treated with absolute ethanol whichpermits, by concentration of the ethanolic extract to dryness, 0.74 g (yield 45%) of 2-cyano-5-pyrimidinylcarbamoyl-beta-alanine to be obtained in the form of a solid having a melting point of 183° C.

The sweetening potency of this compound corresponds approximately, on a weight basis, to 400 (four hundred) times that of sucrose (by comparison with a 2% sucrose solution).

EXAMPLE 6

Synthesis of 2-cyano-5-pyrimidinylthiocarbamoyl-beta-alanine:

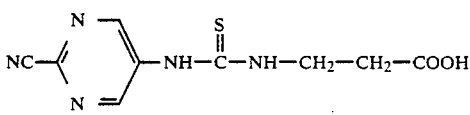

This compound is obtained from beta-alanine and 2-cyano-5-pyrimidinyl isothiocyanate by following the experimental procedure described in Example 2 (yield 13%; melting point 135° C.).

The sweetening potency of this compound corresponds approximately, on a weight basis, to 1000 (one thousand) times that of sucrose (by comparison with a 2% sucrose solution).

EXAMPLE 7:

Synthesis of 5-benzofurazanylcarbamoyl glycine:

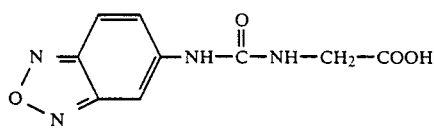

This compound is obtained from glycine and 5benzofurazanyl isocyanate by following the experimental procedure described in Example 2 (yield 68%; melting point 212° C.).

The sweetening potency of this compound corresponds approximately, on a weight basis, to 20 (twenty) times that of sucrose (by comparison with a 2% sucrose solution).

EXAMPLE 8

Synthesis of 5-benzofurazanylcarbamoyl-beta-alanine:

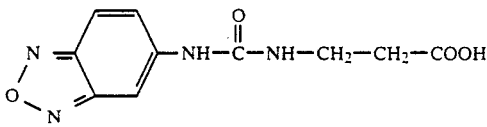

This compound is obtained from beta-alanine and 5-benzofurazanyl isocyanate by following the experimental procedure described in Example 2 (yield 47%; melting point 208° C.).

The sweetening potency of this compound corresponds approximately, on a weight basis, to 800 (eight hundred) times that of sucrose (by comparison with a 2% sucrose solution).

EXAMPLE 9

Synthesis of N-[5benzofurazanylamino(imino)methyl]-2-aminoethanoic acid:

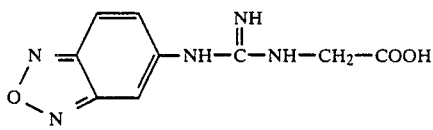

This compound is obtained from 5benzofurazanylthiourea and glycine tert-butyl ester by following the experimental procedure described in Example 3 (yield 25%; melting point 181° C.).

The sweetening potency of this compound corresponds approximately, on a weight basis, to 200 (two hundred) times that of sucrose (by comparison with a 2% sucrose solution).

EXAMPLE 10

Synthesis of N-[cyanoimino(5benzofurazanylamino)methyl]-3-aminopropanoic acid:

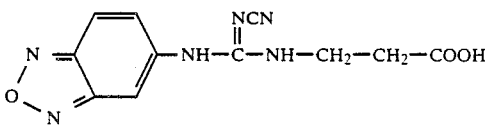

A solution of 1.3 g (4.4 mmol) of 5-benzofurazanylthiocarbamoyl-beta-alanine ethyl ester, 0.371 g (8.8 mmol) of cyanamide, 1.36 g (6.6 mmol) of dicyclohexylcarbodiimide and 0.1 ml of triethylamine in 30 ml of anhydrous acetonitrile is left for 40 hr at room temperature. The mixture is concentrated to dryness. The resulting oil is triturated in ethyl ether (3 × 30 ml). There is obtained 1 g (yield 76%) of a solid which, after purification on a silica column (elution with 90/10 CHCl$_3$/acetone), leads to 0.5 g of ethyl N-[cyanoimino-(5-benzofurazanylamino)methyl]-3-aminopropanoate (melting point of 155° C.).

A solution of 0.5 g (1.65 mmol) of the ester thus obtained and 0.066 g (1.65 mmol) of sodium hydroxide in 15 ml of methanol and 0.1 ml of water is left at room temperature for 30 hr. The mixture is concentrated to dryness. To the residue obtained there is added 10 ml of water, and the residue is purified by washing with dichloromethane (3 × 20 ml). The cooled aqueous phase is acidified with a 3 N hydrochloric acid solution until a pH close to 3 is obtained. The solid obtained is recovered by filtration and then washed by 2 × 3 ml of water. After drying, 0.2 g (yield 44%) of N-[cyanoimino-(5benzofurazanylamino)methyl]-3-aminopropanoic acid is obtained (melting point 92° C.).

The sweetening potency of this compound corresponds approximately, on a weight basis, to 200 (two hundred) times that of sucrose (by comparison with a 2% sucrose solution).

EXAMPLE 11

Synthesis of 1-oxide-5-benzofurazanylcarbamoyl-beta-alanine:

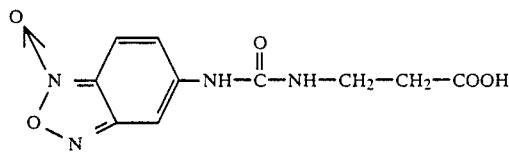

This compound is obtained from beta-alanine and 1-oxide-5-benzofurazanyl isocyanate by following the experimental procedure described in Example 2 (yield 76%; melting point 196° C.).

The sweetening potency of this compound corresponds approximately, on a weight basis, to 500 (five hundred) times that of sucrose (by comparison with a 2% sucrose solution).

EXAMPLE 12

Synthesis of 5-benzothiofurazanylcarbamoyl-beta-alanine:

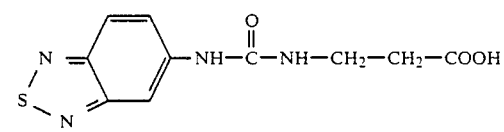

This compound is obtained from beta-alanine and 5-benzothiofurazanyl isocyanate by following the experimental procedure described in Example 2 (yield 47%; melting point 189° C.).

The sweetening potency of this compound corresponds approximately, on a weight basis, to 50 (fifty) times that of sucrose (by comparison with a 2% sucrose solution).

EXAMPLE 13

Synthesis of (1H-indazol-6-yl)thiocarbamoyl-beta-alanine:

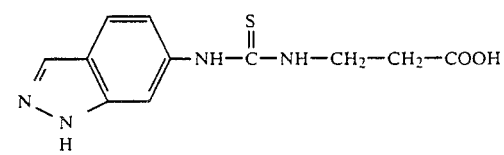

A solution of 5 g (28.6 mmol) of 1H-indazol-6-yl isothiocyanate, 5.3 g (34.3 mmol) of beta-alanine ethyl ester hydrochloride and 4.8 ml (34.3 mmol) of triethylamine in 50 ml of chloroform is left at room temperature under agitation for one hour. The chloroform phase is washed with water (2 × 10 ml) and with a 1 N hydrochloric acid solution (2 × 10 ml). It is dried and concentrated to dryness. The residue (8 g) is triturated in ethyl ether (3 × 20 ml). There is obtained 3.1 g of (1H-indazol-6-yl)thiocarbamoyl-beta-alanine ethyl ester (yield 28%, melting point 145° C.).

A solution of 0.6 g (2.05 mmol) of the ester thus obtained and 0.09 g (2.36 mmol) of sodium hydroxide in 15 ml of methanol and 0.1 ml of water is left at room temperature and under agitation for 20 hr. After concentration to dryness, 10 ml of water is added to the residue is obtained. After purification by extraction with ethyl acetate (3 × 20 ml), the aqueous phase is cooled and then acidified with a 3 N hydrochloric acid solution until a pH close to 3 is obtained 0.293 g (yield 56%) of (1H-indazol-6-yl)thiocarbamoyl-beta-alanine is obtained in the form of a solid having a melting point of 175° C.

The sweetening potency of this compound corresponds approximately, on a weight basis, to 150 (one hundred fifty) times that of sucrose (by comparison with a 2% sucrose solution).

The sweetening potencies obtained with the different compounds cited in Examples 1 to 13 are summarized in Table I hereinafter the sweetening potencies as listed were evaluated, on a weight basis, relative to a 2% sucrose solution

TABLE I $$R-NH-\overset{A}{\underset{\|}{C}}-NH-(CH_2)_n-COOH$$

| Compound | R | A | n | Sweetening potency |
|---|---|---|---|---|
| 1 | pyrazinyl | O | 2 | 50 |
| 2 | Cl-pyrazinyl | O | 2 | 50 |
| 3 | Cl-pyrazinyl | NH | 1 | 50 |
| 4 | NC-pyrazinyl | O | 2 | 700 |
| 5 | NC-pyrazinyl | O | 2 | 400 |
| 6 | NC-pyrazinyl | S | 2 | 1000 |

TABLE I-continued $$R-NH-\overset{\overset{A}{\|}}{C}-NH-(CH_2)_n-COOH$$

| Compound | R | A | n | Sweetening potency |
|---|---|---|---|---|
| 7 | 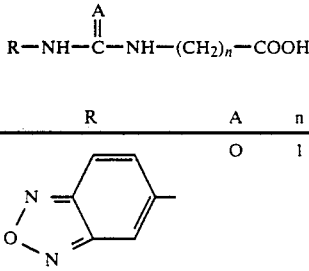 | O | 1 | 20 |
| 8 | 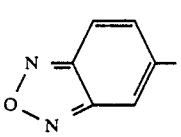 | O | 2 | 800 |
| 9 | 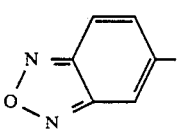 | NH | 1 | 200 |
| 10 | 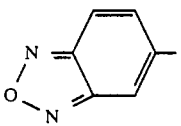 | NCN | 2 | 200 |
| 11 | 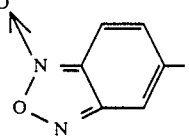 | O | 2 | 500 |
| 12 | 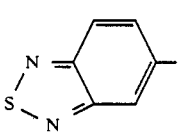 | O | 2 | 50 |
| 13 | 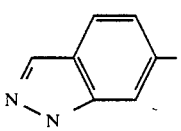 | S | 2 | 150 |

What is claimed is:

1. A sweetening agent of the formula $$R-NH-\overset{\overset{A}{\|}}{C}-NH-(CH_2)_n-B$$

wherein
R is an heterocyclic group selected from the group consisting of

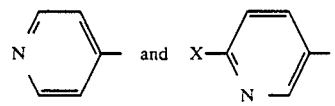

wherein
X is Cl, Cn, or No₂
A is O, S. NH or N—CN, NH being able to be salified in hydrochloride form;
n is 1 or 2; and
B is COOH or a sodium, potassium, ammonium, calcium or magnesium salt.

2. A process for rendering a substance sweet, comprising adding to said substance an adequate quantity of at least one sweetening agent according to claim 1.

3. A substance obtained from the process of claim 2.

4. A sweetening composition, comprising an adequate quantity of at least one sweetening agent according to claim 1 and a carrier or bulking agent selected from the group consisting of polydextrose, starch, maltodextrins, cellulose, methylcellulose, carboxymethylcellulose, hydroxymethylcellulose, microcrystalline cellulose, sodium alginate, pectins, gums, lactose, maltose, glucose, leucine, glycerol, mannitol, sorbitol, sodium bicarbonate, and phosphoric, citric, tartaric, fumaric, benzoic, sorbic and propionic acids, and their sodium, potassium or calcium salts.

5. A sweetening agent, comprising a sweetening agent according to claim 1 and at least one other sweetening agent, the other sweetening agent being selected from the group consisting of sucrose, corn syrup, fructose, aspartame, alitame, neohesperidin dihydrochalcone, hydrogenated isomaltulose, stevioside, L-sugars, glycyrrhizin, xylitol, sorbitol, mannitol, acesulfame-K, saccharin and its sodium, potassium, ammonium or calcium salts, cyclamic acid and its sodium, potassium, ammonium or calcium salts, trichlorogalactosucrose, monellin and thaumtin.

6. A sweetening agent according to claim 1, wherein:
R is 2-cyanopyrid-5-yl;
A is O or NH;
n is 1 when A is NH or 2 when A is O.

7. A process for sweetening a product for which a sweet taste is desirable, said product being selected from the group consisting of foods, beverages, confectioneries, pastries, chewing gum, hygiene products, cosmetics, toiletries, pharmaceutical or veterinary products, comprising adding to such product an adequate quantity of at least one sweetening agent of claim 1.

8. A product obtained from the process of claim 7.

9. A sweetening agent selected from the group consisting of:
4-pyridylcarbamoyl-beta-alanine;
2-chloro-5-pyridylcarbamoyl-beta-alanine;
N-[2-chloro-5-aminopyridyl(imino)methyl]-2-aminoethanoic acid;
and
2-cyano-5-pyridylcarbamoyl-beta-alanine.